United States Patent
Zhang et al.

(10) Patent No.: US 11,414,415 B2
(45) Date of Patent: Aug. 16, 2022

(54) 6H-IMIDAZO[4,5,1-IJ]QUINOLONE, SYNTHESIS METHOD AND USE THEREOF

(71) Applicant: HANGZHOU NORMAL UNIVERSITY, Hangzhou (CN)

(72) Inventors: Pengfei Zhang, Hangzhou (CN); Wei Huang, Hangzhou (CN); Chao Shen, Hangzhou (CN); Jun Xu, Hangzhou (CN); Jiabin Shen, Hangzhou (CN); Weiming Xu, Hangzhou (CN)

(73) Assignee: HANGZHOU NORMAL UNIVERSITY, Hangzhou (CN)

( * ) Notice: Subject to any disclaimer, the term of this patent is extended or adjusted under 35 U.S.C. 154(b) by 96 days.

(21) Appl. No.: 16/906,017

(22) Filed: Jun. 19, 2020

(65) Prior Publication Data

US 2021/0332038 A1 Oct. 28, 2021

(30) Foreign Application Priority Data

Apr. 23, 2020 (CN) .......................... 202010327811.8

(51) Int. Cl.
| | | |
|---|---|---|
| C07D 215/00 | (2006.01) | |
| C07D 221/00 | (2006.01) | |
| C07D 409/04 | (2006.01) | |
| C07D 471/04 | (2006.01) | |
| B01J 23/72 | (2006.01) | |
| C07D 215/40 | (2006.01) | |

(52) U.S. Cl.
CPC ............ *C07D 471/04* (2013.01); *B01J 23/72* (2013.01); *C07D 215/40* (2013.01)

(58) Field of Classification Search
CPC .. C07D 215/00; C07D 221/00; C07D 409/04; A61P 35/00
See application file for complete search history.

*Primary Examiner* — Bruck Kifle
(74) *Attorney, Agent, or Firm* — . W&G Law Group (57) ABSTRACT

The present invention relates to the technical field of chemical synthesis of pharmaceutical chemicals, and provides a 6H-imidazo[4,5,1-ij]quinolone, a synthesis method and use thereof. 6H-imidazo[4,5,1-ij]quinolone derivatives provided by the present invention are a novel group of active quinolone derivatives, which have tumor cell inhibition activity and exhibit $IC_{50}$ values equivalent to anti-lung cancer drug osimertinib; these quinolone derivatives have a broad application prospect in the preparation of antitumor drugs. The 6H-imidazo[4,5,1-ij]quinolone provided by the present invention is of high research and application value and has potential application prospects in fields of pharmaceutical chemicals, materials, dyes, etc. The present invention uses thioquinolinamide as a raw material to synthesize 6H-imidazo[4,5,1-ij]quinolones, featuring simple operation, excellent selectivity, high yield, mild reaction conditions, and easy product separation.

13 Claims, 3 Drawing Sheets

6H-IMIDAZO[4,5,1-IJ]QUINOLONE, SYNTHESIS METHOD AND USE THEREOF

TECHNICAL FIELD

The present invention relates to the technical field of chemical synthesis of pharmaceutical chemicals, and in particular to a 6H-imidazo[4,5,1-ij]quinolone, a synthesis method and use thereof.

BACKGROUND

Quinolone is a framework structure of a plurality of active drug molecules, and more than 10,000 quinolone derivatives have been reported to date. Quinolone derivatives, as a hotspot of drug development, have antibacterial, antituberculotic, antimalarial, and antiviral activities. Because antibacterial mechanism thereof is inhibition of DNA gyrase, many novel quinolones possess excellent antitumor activity simultaneously (J. Heterocyclic Chem., 2018, 55, 1854). So far, research in this field still focuses on the investigation of novel quinolone derivatives to improve application value thereof.

SUMMARY

In view of this, the present invention provides a 6H-imidazo[4,5,1-ij]quinolone derivative, a synthesis method and use thereof. The 6H-imidazo[4,5,1-ij]quinolone derivative provided by the present invention is a novel active quinolone derivative, having high research and application value.

In order to achieve the above objective, the present invention provides the following technical solution:

a 6H-imidazo[4,5,1-ij]quinolone, having a structural formula as shown in formula I:

formula I where: $R^1$ is alkyl, aryl, substituted aryl, or thienyl; $R^2$ is hydrogen, halogen, nitro, C1-C5 alkoxy, or C3-C5 alkyl.

Preferably, when the $R^1$ in formula I is alkyl, the alkyl is linear alkyl or cycloalkyl; when the $R^1$ in formula I is substituted aryl, the substituted aryl is 4-methylphenyl, 4-fluorophenyl, or 2-chlorophenyl.

Preferably, the cycloalkyl is cyclopropyl.

The present invention provides a synthesis method of the above 6H-imidazo[4,5,1-ij]quinolone, including the following steps:

cyclizing thioquinolinamide with a structure of formula II in the presence of copper salt and oxidant, to obtain the 6H-imidazo[4,5,1-ij]quinolone with the structure of formula I;

formula II

Preferably, a molar ratio of the copper salt to the thioquinolinamide with the structure of formula II is (0.01-0.5):1.

Preferably, the copper salt is one or more of cupric bromide, copper chloride, cuprous iodide, cuprous bromide, cuprous chloride, copper acetate, copper oxide, and cuprous oxide.

Preferably, the oxidant is one or more of (diacetoxyiodo)benzene, [bis(trifluoroacetoxy)iodo]benzene, peroxyacetic acid, potassium persulfate, sodium persulfate, and ammonium persulfate; a molar ratio of the oxidant to the thioquinolinamide with the structure of formula II is (0.5-10):1.

Preferably, the cyclization is conducted at 0-100° C. for 1-10 h.

Preferably, a solvent for the cyclization is one or more of benzene, toluene, xylene, chlorobenzene, acetonitrile, tetrahydrofuran, dichloromethane, chloroform, dichloroethane, and ethyl acetate.

The present invention further provides use of the above 6H-imidazo[4,5,1-ij]quinolone in the preparation of antitumor drugs.

The present invention provides a 6H-imidazo[4,5,1-ij]quinolone, having a structural formula as shown in formula I. The 6H-imidazo[4,5,1-ij]quinolone derivatives provided by the present invention is a novel active quinolone derivative, which has tumor cell inhibition activity and exhibits $IC_{50}$ values equivalent to anti-lung cancer drug osimertinib; the quinolone derivative is of high research and application value and have potential application prospects in fields of pharmaceutical chemicals, materials, dyes, etc.

The present invention provides a synthesis method of the above 6H-imidazo[4,5,1-ij]quinolone. The present invention uses thioquinolinamide with the structure of formula II as a raw material to synthesize the 6H-imidazo[4,5,1-ij]quinolone of the present invention, featuring simple operation, excellent selectivity, high yield, mild reaction conditions, and easy product separation.

The present invention further provides use of the above 6H-imidazo[4,5,1-ij]quinolone in the preparation of antitumor drugs. The 6H-imidazo[4,5,1-ij]quinolone provided by the present invention has tumor cell inhibition activity and has a broad application prospect in the preparation of antitumor drugs.

DETAILED DESCRIPTION

The present invention provides a 6H-imidazo[4,5,1-ij]quinolone, having a structural formula as shown in formula I:

formula I where: $R^1$ is alkyl, aryl, substituted aryl, or thienyl; the alkyl is preferably linear alkyl or cycloalkyl; the cycloalkyl is preferably cyclopropyl; the substituted aryl is preferably 4-methylphenyl, 4-fluorophenyl, or 2-chlorophenyl; $R^2$ is hydrogen, halogen, nitro, C1-C5 alkoxy, or C3-C5 alkyl.

The present invention further provides a synthesis method of the above 6H-imidazo[4,5,1-ij]quinolone, including the following steps:

cyclizing thioquinolinamide with a structure of formula II in the presence of copper salt and oxidant, to obtain the 6H-imidazo[4,5,1-ij]quinolone with the structure of formula I;

formula II types of $R^1$ and $R^2$ in formula II are consistent with those in formula I, and the details will not be repeated herein. The present invention has no special requirement for sources of the thioquinolinamide with the structure of formula II, as long as preparation methods thereof are well known to those skilled in the art.

In the present invention, the copper salt is preferably one or more of cupric bromide, copper chloride, cuprous iodide, cuprous bromide, cuprous chloride, copper acetate, copper oxide, and cuprous oxide; a molar ratio of the copper salt to the thioquinolinamide with the structure of formula II is preferably (0.01-0.5):1, and more preferably (0.1-0.2):1; the copper salt functions as a catalyst.

In the present invention, the oxidant is preferably one or more of (diacetoxyiodo)benzene, [bis(trifluoroacetoxy)iodo]benzene, peroxyacetic acid, potassium persulfate, sodium persulfate, and ammonium persulfate; a molar ratio of the oxidant to the thioquinolinamide with the structure of formula II is preferably (0.5-10):1, and more preferably (2-5):1.

In the present invention, a solvent for the cyclization is preferably one or more of benzene, toluene, xylene, chlorobenzene, acetonitrile, tetrahydrofuran, dichloromethane, chloroform, dichloroethane, and ethyl acetate. The present invention has no special requirement for consumption of the solvent, as long as the cyclization is allowed to conduct successfully.

In specific examples of the present invention, preferably, the thioquinolinamide with the structure of formula II, the copper salt, and the oxidant are charged into a reaction flask and dissolved in the solvent.

In the present invention, the cyclization is preferably conducted at 0-100° C., more preferably 20-50° C., and further preferably 25-35° C.; the cyclization preferably lasts for 1-10 h, and more preferably 3-5 h.

In the present invention, the cyclization has a reaction formula as shown in formula a:

formula a

After reaching the cyclization time, the present invention preferably adds a saturated sodium bicarbonate solution to a reaction solution to quench the reaction, and subsequently conducts post-treatment on the resulting product mixture. In the present invention, the post-treatment preferably includes the following steps: allowing the resulting product mixture to stand for separation into layers; drying the resulting organic phase, filtering and concentrating successively, to obtain a crude solid product; and recrystallizing the crude solid product to obtain a 6H-imidazo[4,5,1-ij]quinolone. In the present invention, a desiccant for drying the organic phase is preferably anhydrous magnesium sulfate or anhydrous sodium sulfate; a solvent for the recrystallization is preferably a mixed solvent of ethyl acetate and petroleum ether, and a volume ratio of the ethyl acetate to the petroleum ether in the mixed solvent is preferably 1:1.

The present invention further provides use of the 6H-imidazo[4,5,1-ij]quinolone according to the above solution or the 6H-imidazo[4,5,1-ij]quinolone synthesized the synthesis method according to the above solution in the preparation of antitumor drugs. The 6H-imidazo[4,5,1-ij]quinolone provided by the present invention has tumor cell inhibition activity and has a broad application prospect in the preparation of antitumor drugs. The present invention has no special requirement for how to use specifically, as long as the use is well known to those skilled in the art.

The technical solution in the present invention will be clearly and completely described below in conjunction with the examples of the present invention.

Example 1

Figure 1:
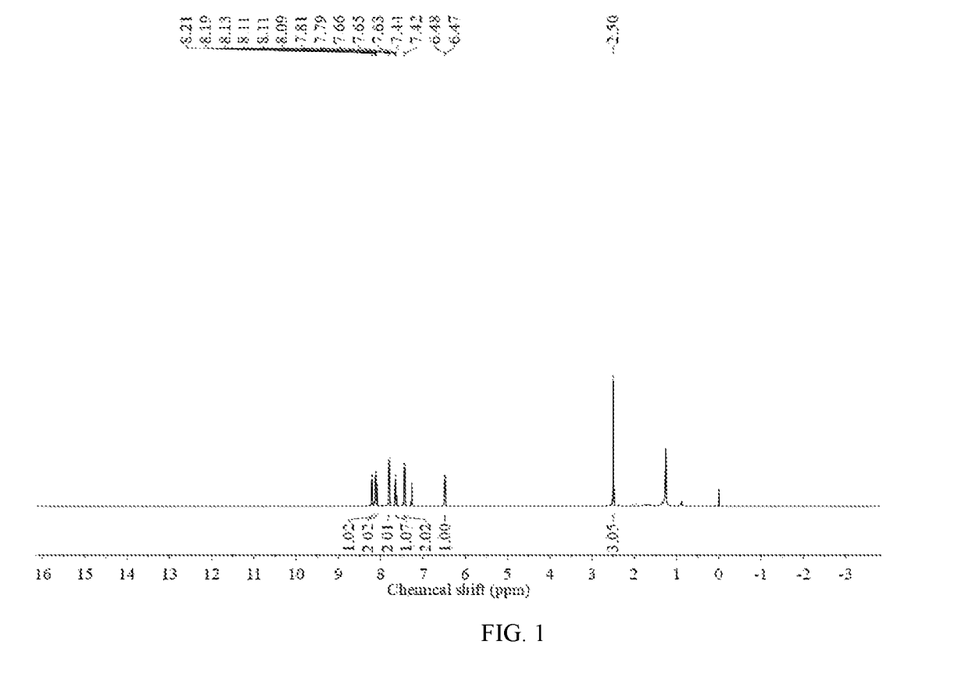
FIG. 1 is an $^1$H NMR spectrum of a 6H-imidazo[4,5,1-ij]quinolone with a structure of formula I-a prepared in Example 1.

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (12.90 g, 30 mmol), and copper chloride (0.014 g, 0.1 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.30 g of white solid (I-a), with a yield of 50% and a melting point of 156-157° C. $^1$H NMR (500 MHz, CDCl$_3$) δ 8.20 (d, J=7.9 Hz, 1H), 8.11 (dd, J=10.6, 7.9 Hz, 2H), 7.80 (d, J=8.0 Hz, 2H), 7.65 (t, J=7.8 Hz, 1H), 7.43 (d, J=7.9 Hz, 2H), 6.48 (d, J=7.9 Hz, 1H), 2.50 (s, 3H). $^1$H-NMR spectrum of the product is illustrated in FIG. 1.

Example 2

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (12.90 g, 30 mmol), and copper chloride (0.675 g, 5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.95 g of white solid (I-a), with a yield of 75%.

Example 3

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (12.90 g, 30 mmol), cupric bromide (0.11 g, 0.5 mmol), copper acetate (0.09 g, 0.5 mmol), and cuprous oxide (0.07 g, 0.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.43 g of white solid (I-a), with a yield of 55%.

Example 4

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (2.15 g, 5 mmol), and copper chloride (0.20 g, 1.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.07 g of white solid (I-a), with a yield of 41%.

Example 5

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (43.0 g, 100 mmol), and copper chloride (0.20 g, 1.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.79 g of white solid (I-a), with a yield of 69%.

Example 6

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (3.22 g, 10 mmol), potassium persulfate (2.70 g, 10 mmol), ammonium persulfate (2.28 g, 10 mmol), and copper chloride (0.20 g, 1.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.38 g of white solid (I-a), with a yield of 53%.

Example 7

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 4 h under stirring at 0° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.69 g of white solid (I-a), with a yield of 65%.

Example 8

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 4 h under stirring at 100° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.98 g of white solid (I-a), with a yield of 76%.

Example 9

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 1 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 0.65 g of white solid (I-a), with a yield of 25%.

Example 10

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 10 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.92 g of white solid (I-a), with a yield of 74%.

Example 11

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (12.90 g, 30 mmol), and copper chloride (0.20 g, 1.5 mmol) were charged into a reaction flask and dissolved in a mixed solvent of benzene (10 mL), acetonitrile (5 mL), and ethyl acetate (5 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.56 g of white solid (I-a), with a yield of 60%.

Example 12

6H-imidazo[4,5,1-ij]quinolone with a structure of formula I-a was synthesized according to the following reaction formula:

4-Methylphenylthioquinolinamide (II-a) (2.78 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 2.13 g of white solid (I-a), with a yield of 82%.

Example 13

Figure 2:
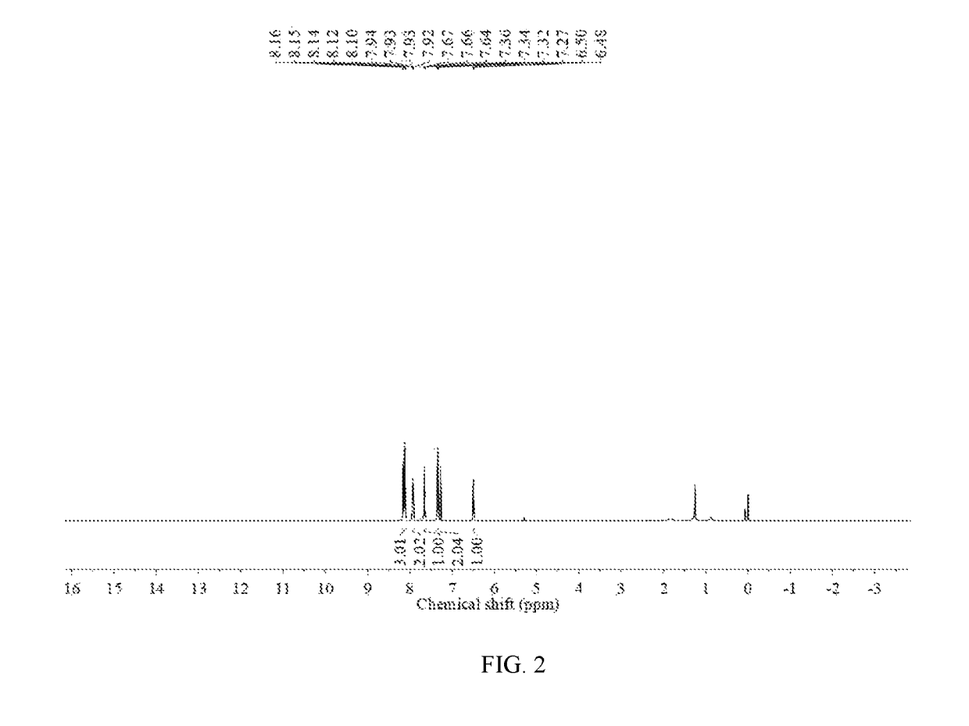
FIG. 2 is an $^1$H NMR spectrum of a 6H-imidazo[4,5,1-ij]quinolone with a structure of formula I-b prepared in Example 13.

6H-imidazo[4,5,1-ij]quinolone with a structure of formula I-b was synthesized according to the following reaction formula:

4-Fluorophenylthioquinolinamide (II-b) (2.82 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 2.05 g of white solid (I-b), with a yield of 78% and a melting point of 146-148° C. $^1$H NMR (500 MHz, CDCl$_3$) δ 8.18-8.08 (m, 3H), 7.93 (dd, J=8.4, 5.2 Hz, 2H), 7.66 (t, J=7.8 Hz, 1H), 7.34 (t, J=8.4 Hz, 2H), 6.49 (d, J=7.8 Hz, 1H). $^1$H NMR spectrum of the product is illustrated in FIG. 2.

Example 14

Figure 3:
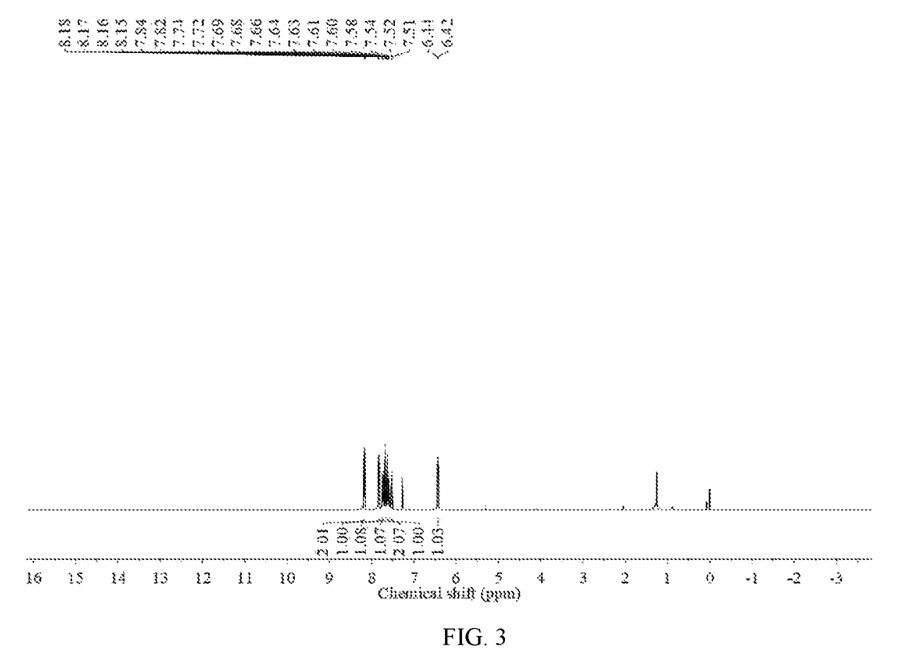
FIG. 3 is an $^1$H NMR spectrum of a 6H-imidazo[4,5,1-ij]quinolone with a structure of formula I-c prepared in Example 14.

6H-imidazo[4,5,1-ij]quinolone with a structure of formula I-c was synthesized according to the following reaction formula:

2-Chlorophenylthioquinolinamide (II-c) (2.98 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 2.29 g of white solid (I-c), with a yield of 82% and a melting point of 108-109° C. $^1$H NMR (500 MHz, CDCl$_3$) δ 8.17 (dd, J=7.8, 5.0 Hz, 2H), 7.83 (d, J=7.8 Hz, 1H), 7.73 (d, J=8.9 Hz, 1H), 7.68 (t, J=7.8 Hz, 1H), 7.65-7.57 (m, 2H), 7.52 (t, J=7.4 Hz, 1H), 6.43 (d, J=7.8 Hz, 1H). $^1$H NMR spectrum of the product is illustrated in FIG. 3.

Example 15

6H-imidazo[4,5,1-ij]quinolone with a structure of formula I-d was synthesized according to the following reaction formula:

-continued

I-d

Figure 4:
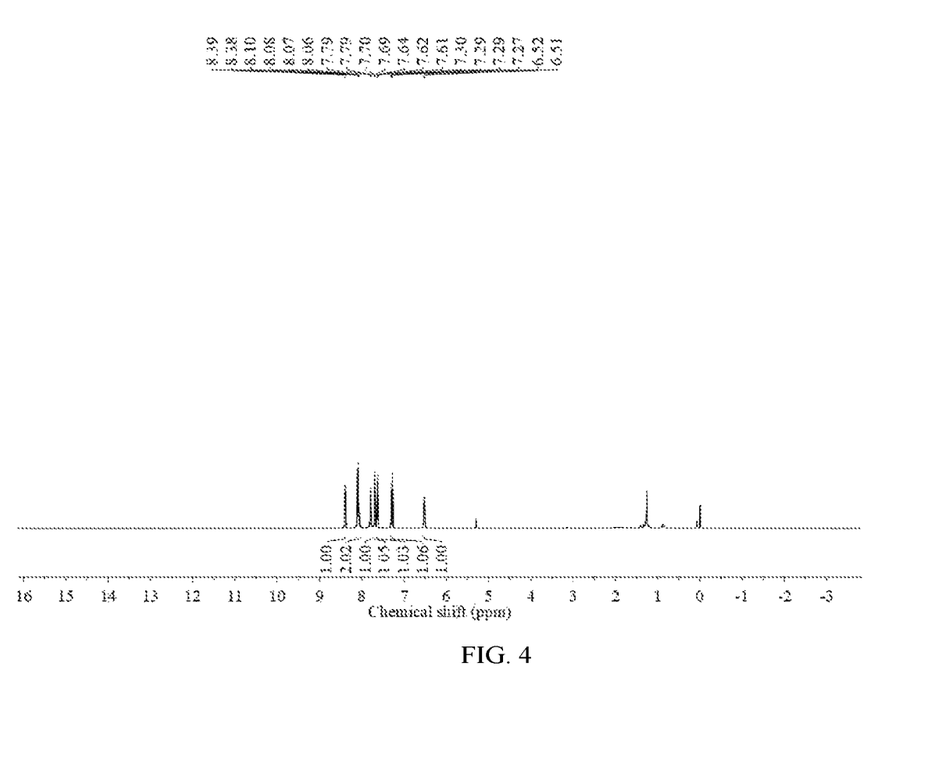
FIG. 4 is an $^1$H NMR spectrum of a 6H-imidazo[4,5,1-ij]quinolone with a structure of formula I-d prepared in Example 15.

Thiophene-2-thioquinolinamide (II-d) (2.70 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 2.06 g of white solid (IV-d), with a yield of 82% and a melting point of 122-123° C. $^1$H NMR (500 MHz, CDCl$_3$) δ 8.39 (d, J=7.8 Hz, 1H), 8.08 (dd, J=12.9, 7.7 Hz, 2H), 7.79 (d, J=2.8 Hz, 1H), 7.69 (d, J=5.0 Hz, 1H), 7.62 (t, J=7.7 Hz, 1H), 7.34-7.27 (m, 1H), 6.52 (d, J=7.7 Hz, 1H). $^1$H NMR spectrum of the product is illustrated in FIG. 4.

Example 16

6H-imidazo[4,5,1-ij]quinolone with a structure of formula I-e was synthesized according to the following reaction formula:

II-e

I-e

Figure 5:
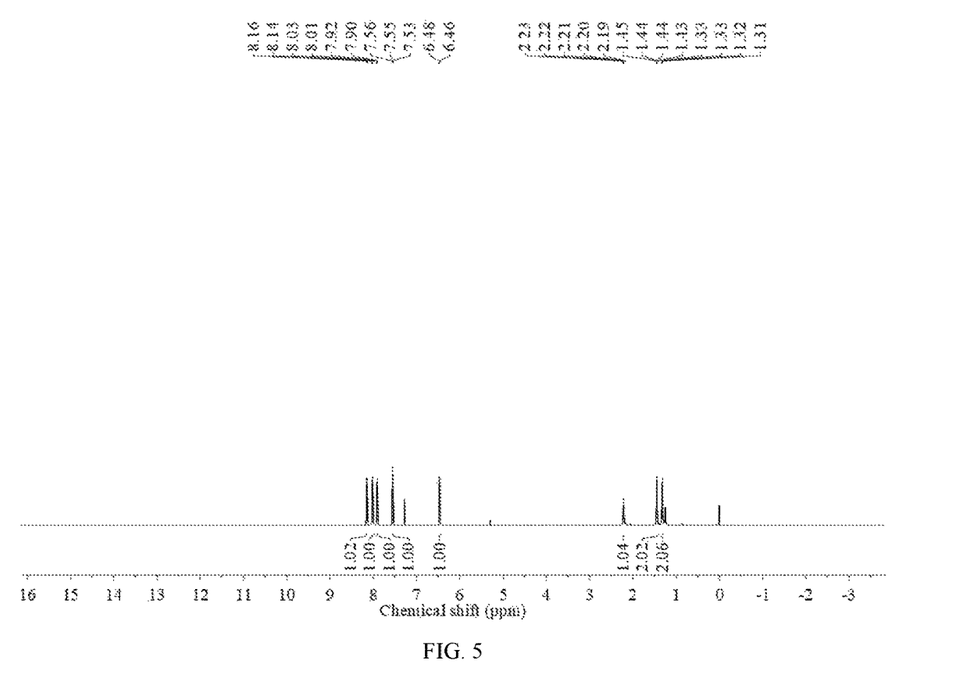
FIG. 5 is an $^1$H NMR spectrum of a 6H-imidazo[4,5,1-ij]quinolone with a structure of formula I-e prepared in Example 16.

Cyclopropylthioquinolinamide (II-e) (2.28 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 1.59 g of white solid (I-e), with a yield of 76% and a melting point of 114-116° C. $^1$H NMR (500 MHz, CDCl$_3$) δ 8.15 (d, J=7.8 Hz, 1H), 8.02 (d, J=7.9 Hz, 1H), 7.91 (d, J=7.7 Hz, 1H), 7.55 (t, J=7.8 Hz, 1H), 6.47 (d, J=7.8 Hz, 1H), 2.24-2.18 (m, 1H), 1.44 (dd, J=4.6, 2.7 Hz, 2H), 1.32 (dd, J=8.1, 2.9 Hz, 2H). $^1$H NMR spectrum of the product is illustrated in FIG. 5.

Example 17

6H-imidazo[4,5,1-ij]quinolone with a structure of formula I-f was synthesized according to the following reaction formula:

II-f

I-f

Figure 6:
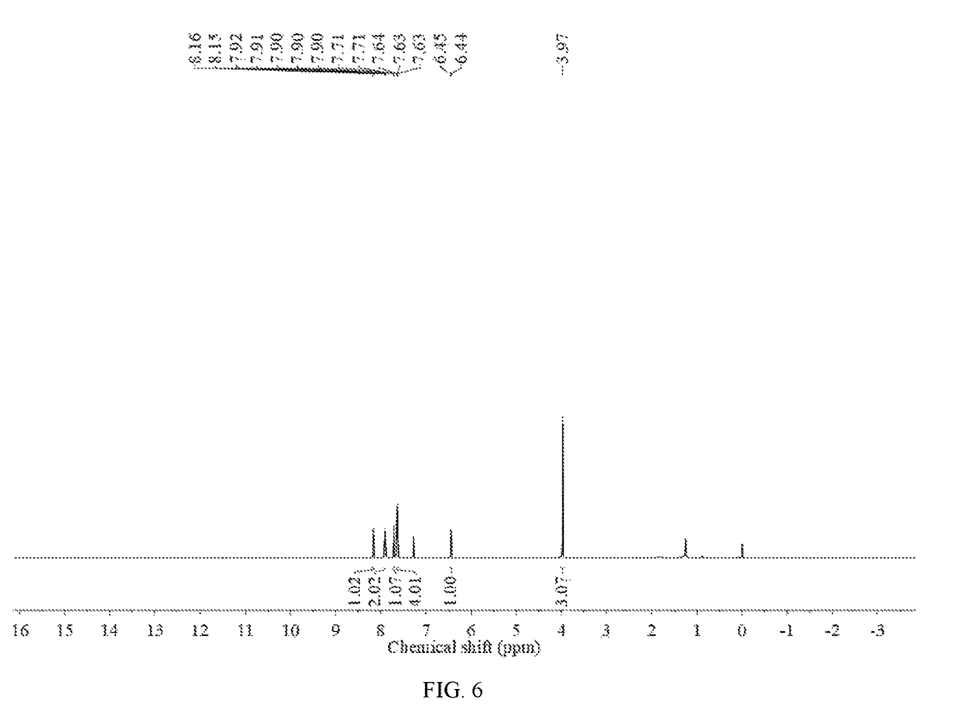
FIG. 6 is an $^1$H NMR spectrum of a 6H-imidazo[4,5,1-ij]quinolone with a structure of formula I-f prepared in Example 17.

Phenylthio-6-methoxyquinolinamide (II-f) (2.94 g, 10 mmol), [bis(trifluoroacetoxy)iodo]benzene (12.90 g, 30 mmol), and copper chloride (0.20 g, 1.5 mmol) were charged into a reaction flask and dissolved in chloroform (20 mL); the mixture reacted for 4 h under stirring at 35° C.; after reaction, the reaction was quenched with saturated sodium bicarbonate solution (10 mL); after stirring fully, the mixture was allowed to stand for separation into layers; organic layer was dried with anhydrous magnesium sulfate, filtered, and concentrated to obtain a crude solid product; the crude product was recrystallized with ethyl acetate/petroleum ether (v/v=1:1) to obtain 2.07 g of white solid (I-f), with a yield of 75% and a melting point of 121-122° C. $^1$H NMR (500 MHz, CDCl$_3$) δ 8.15 (d, J=7.8 Hz, 1H), 7.94-7.88 (m, 2H), 7.71 (d, J=1.9 Hz, 1H), 7.67-7.59 (m, 4H), 6.44 (d, J=7.8 Hz, 1H), 3.97 (s, 3H). $^1$H NMR spectrum of the product is illustrated in FIG. 6.

Example 18

Biological activity assay was conducted on compounds I-d to I-f prepared in the above examples:

with A549 (a lung cancer cell) as a subject, cell growth was observed in the presence of 6H-imidazo[4,5,1-ij]quinolones as shown in formulas I-d to I-f, and tumor cell proliferation was assayed by MTT assay. Original osimertinib was used as control.

Specific procedure was as follows: plating A549 cells in a 96-well plate at a cell density of $2 \times 10^4$ cells/mL; after placing in an incubator overnight at 37° C. in 5% $CO_2$, adding samples to be screened (sample concentrations are given in Table 1; medication groups were given 10 μL of the drug at the corresponding concentration per well, and blank control group was given 10 μL of PBS per well); after culturing for 44 h, adding 10 μL of MTT per well to culture for additional 4 h; dissolving in DMSO, shaking, and detecting on a microplate reader at 570 nm.

Inhibitory concentration 50 ($IC_{50}$) values of 6H-imidazo[4,5,1-ij]quinolone derivatives with structures as shown in formulas I-d to I-f and control drug original osimertinib against A549 (lung cancer cell) were detected. Detection results are listed in Table 1.

TABLE 1

Results of the biological activity assay

| Cell | Drug | Concentration (water as solvent) | $IC_{50}$ (μmol/L) |
|---|---|---|---|
| A549 | I-a | 0.5 mg/mL | 11.156 |
| | I-b | 0.5 mg/mL | 15.321 |
| | I-c | 0.5 mg/mL | 16.157 |
| | I-d | 0.5 mg/mL | 9.899 |
| | I-e | 0.5 mg/mL | 21.121 |
| | I-f | 0.5 mg/mL | 12.345 |
| | Osimertinib | 0.5 mg/mL | 9.742 |

As shown in Table, all 6H-imidazo[4,5,1-ij]quinolone derivatives synthesized by the present invention have A549 cell (lung cancer cell) inhibition activity, of which compound I-d exhibits an $IC_{50}$ value equivalent to anti-lung cancer drug osimertinib.

The above descriptions are merely preferred implementations of the present invention. It should be noted that a person of ordinary skill in the art may further make several improvements and modifications without departing from the principle of the present invention, but such improvements and modifications should be deemed as falling within the protection scope of the present invention.

What is claimed is:

1. A compound of formula I:

formula I wherein: $R^1$ is linear alkyl or cycloalkyl; aryl; 4-methylphenyl, 4-fluorophenyl, or 2-chlorophenyl; or thienyl; and $R^2$ is hydrogen, halogen, nitro, C1-C5 alkoxy, or C3-C5 alkyl.

2. The compound of claim 1, wherein the cycloalkyl is cyclopropyl.

3. A process for producing a compound of formula I according to claim 1, comprising:
cyclizing a compound of formula II in the presence of copper salt and oxidant, to obtain the compound of formula I formula II 4. The process of claim 3, wherein a molar ratio of the copper salt to the compound of formula II is (0.01-0.5):1.

5. The process of claim 3, wherein the copper salt is one or more copper salts selected from the group consisting of cupric bromide, copper chloride, cuprous iodide, cuprous bromide, cuprous chloride, copper acetate, copper oxide, and cuprous oxide.

6. The process of claim 3, wherein the oxidant is one or more oxidants selected from the group consisting of (diacetoxyiodo)benzene, [bis(trifluoroacetoxy)iodo]benzene, peroxyacetic acid, potassium persulfate, sodium persulfate, and ammonium persulfate; a molar ratio of the oxidant to the compound of formula II is (0.5-10):1.

7. The process of claim 3, wherein the cyclization is conducted at 0-100° C. for 1-10 h.

8. The process of claim 3, wherein a solvent for the cyclization is one or more solvents selected from the group consisting of benzene, toluene, xylene, chlorobenzene, acetonitrile, tetrahydrofuran, dichloromethane, chloroform, dichloroethane, and ethyl acetate.

9. A process for producing a compound of formula I according to claim 2, comprising:
cyclizing a compound of formula II in the presence of copper salt and oxidant, to obtain the compound of formula I formula II 10. The process of claim 9, wherein a molar ratio of the copper salt to the compound of formula II is (0.01-0.5):1.

11. The process of claim 4, wherein the copper salt is one or more copper salts selected from the group consisting of cupric bromide, copper chloride, cuprous iodide, cuprous bromide, cuprous chloride, copper acetate, copper oxide, and cuprous oxide.

12. The process of claim 9, wherein the oxidant is one or more oxidants selected from the group consisting of (diacetoxyiodo)benzene, [bis(trifluoroacetoxy)iodo]benzene, peroxyacetic acid, potassium persulfate, sodium persulfate, and ammonium persulfate; a molar ratio of the oxidant to the compound of formula II is (0.5-10):1.

13. The process of claim 4, wherein the cyclization is conducted at 0-100° C. for 1-10 h.

\* \* \* \* \*